(12) United States Patent
Mayeresse et al.

(10) Patent No.: US 8,409,587 B2
(45) Date of Patent: *Apr. 2, 2013

(54) IMMUNOGENIC COMPOSITION

(75) Inventors: Yves Mayeresse, Rixensart (BE); Jean Stephenne, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 681 days.

This patent is subject to a terminal disclaimer.

(21) Appl. No.: 10/533,464

(22) PCT Filed: Oct. 30, 2003

(86) PCT No.: PCT/EP03/12160
§ 371 (c)(1),
(2), (4) Date: Mar. 3, 2006

(87) PCT Pub. No.: WO2004/039399
PCT Pub. Date: May 13, 2004

(65) Prior Publication Data
US 2006/0127414 A1 Jun. 15, 2006

(30) Foreign Application Priority Data

| Nov. 1, 2002 | (GB) | 0225520.6 |
| Nov. 1, 2002 | (GB) | 0225532.1 |
| Nov. 1, 2002 | (GB) | 0225543.8 |
| Jul. 24, 2003 | (GB) | 0317371.3 |
| Jul. 24, 2003 | (GB) | 0317380.4 |
| Jul. 24, 2003 | (GB) | 0317381.2 |

(51) Int. Cl.
*A61K 39/295* (2006.01)
*A61K 39/187* (2006.01)
(52) U.S. Cl. ........... 424/201.1; 424/216.1; 424/256.1
(58) Field of Classification Search ............ None
See application file for complete search history.

(56) References Cited

U.S. PATENT DOCUMENTS

| 3,767,790 | A | 10/1973 | Guttag | 424/81 |
| 5,149,653 | A | 9/1992 | Roser | |
| 5,176,909 | A | 1/1993 | Nerome et al. | |
| 5,795,994 | A | 8/1998 | Kalfa et al. | |
| 6,051,238 | A * | 4/2000 | Volkin et al. | 424/212.1 |
| 7,135,180 | B2 * | 11/2006 | Truong-Le | 424/184.1 |
| 7,927,858 | B2 * | 4/2011 | Mayeresse | 435/243 |
| 8,173,411 | B2 * | 5/2012 | Mayeresse | 435/243 |
| 2003/0180316 | A1 * | 9/2003 | Boutriau et al. | 424/190.1 |
| 2006/0127415 | A1 * | 6/2006 | Mayeresse | 424/234.1 |
| 2007/0298052 | A1 * | 12/2007 | Mayeresse | 424/217.1 |
| 2011/0159038 | A1 * | 6/2011 | Mayeresse | 424/217.1 |

FOREIGN PATENT DOCUMENTS

| EP | 0594950 A1 | 5/1994 |
| EP | 0 775 494 | 5/1997 |
| EP | 0775909 A1 | 5/1997 |
| GB | 989 077 | 4/1965 |
| IL | 122588 | 12/2001 |
| IL | 153506 | 6/2009 |
| PL | 174130 B1 | 5/1994 |
| WO | 9313202 | 7/1993 |
| WO | 9317712 | 9/1993 |
| WO | 9318150 | 9/1993 |
| WO | 9324148 | 9/1993 |
| WO | 9629412 | 9/1996 |
| WO | WO96/40242 | 12/1996 |
| WO | WO-9640077 A2 | 12/1996 |
| WO | WO97/00697 | 1/1997 |
| WO | WO-9729773 A | 8/1997 |
| WO | WO-9800167 A | 1/1998 |
| WO | 9804702 | 5/1998 |
| WO | 9842721 | 10/1998 |
| WO | 9848525 | 10/1998 |
| WO | 9858668 | 12/1998 |
| WO | WO-9913906 A | 3/1999 |
| WO | 9927105 | 6/1999 |
| WO | 9936544 | 7/1999 |
| WO | 9948525 | 9/1999 |
| WO | 9928475 | 10/1999 |
| WO | 9953310 | 10/1999 |
| WO | 9957280 | 11/1999 |
| WO | 0022430 | 4/2000 |
| WO | 0027994 | 5/2000 |
| WO | 0057906 | 5/2000 |
| WO | 0037494 | 6/2000 |
| WO | 0056360 | 9/2000 |
| WO | 0061761 | 10/2000 |
| WO | 0141800 | 6/2001 |
| WO | 0152885 | 7/2001 |
| WO | 0164920 | 7/2001 |
| WO | 0164922 | 7/2001 |
| WO | 0205846 A1 | 1/2002 |
| WO | WO 02/00249 A2 * | 1/2002 |
| WO | 0234771 | 2/2002 |
| WO | 02002606 | 10/2002 |
| WO | WO03/009869 | 2/2003 |
| WO | WO2004/039417 | 5/2004 |
| WO | WO2005/105978 | 11/2005 |

OTHER PUBLICATIONS

Kurikka et al., Comparison of five different vaccination schedules with Haemophilus influenzae type b-tetanus toxoid conjugate vaccine, 1996, The Journal of Pediatrics, vol. 128, No. 4, pp. 524-530.*

(Continued)

*Primary Examiner* — Benjamin P Blumel
(74) *Attorney, Agent, or Firm* — Eric J. Kron

(57) ABSTRACT

The present invention relates to immunogenic compositions comprising a dried solid or highly viscous liquid formulation of inactivated polio virus (IPV) and a stabilizing agent wherein the IPV retains its antigenicity and/or immunogenicity. Methods of producing a dried formulation of IPV which retains its antigenicity/immunogenicity are described.

13 Claims, 3 Drawing Sheets

OTHER PUBLICATIONS

Berge et al., Preservation of Enteroviruses by Freeze-Drying, 1971, Applied Microbiology, vol. 22, No. 5, pp. 850-853.*
Shiomi et al., "Studies on Lyophilization of Sabin Vaccine: 1. Investigation of Fundamental Conditions for Lyophilization". *Database Embase 'Online!*Database Accession No. EMB-1998024433.
Shiomi et al., "Studies on Lyophilization of Sabin Vaccine: 2. Investigation on Long Time Incubation at High and Low Temperatures of Lyophilized Sabin Vaccine". *Database Embase 'Online!*Database Accession No. EMB-1999044367.
Database WPI. Secion Ch, Week 199740. Derwent Publications Ltd. Class A96, AN 1997-434713.
Schmitt et al., "Primary Vaccination of Infants with Diphtheria-Tetanus-Acellular Pertussis-Hepatitis B Virus—Inactivated Polio Virus and Haemophilus Influenzae type B Vaccines Given as Either Separate or Mixed Injections". *The Journal of Pediatrics*, 137(3): 304-312.
*Drying a Biological Product or Vaccine with Disaccharide*. Biotechnol. News, 13(14):5, (1993).
Worrall, et al., *Xerovac: An Ultra Rapid Method for the Dehydration and Preservation of Live Attenuated Rinderpest and Peste des Petits Ruminants Vaccines*, Vaccine, vol. 19, pp. 834-839 (2001).
Kadam, et al., *Effect of Excipients on Product Characteristics and Structure of Lyophilized Lasota Vaccine*, Indian J. Biotechnology, vol. 4, pp. 106-114 (2005).
Ananthanarayan and Paniker, *Textbook of Microbiology*, Seventh Edition, Chapter 48, pp. 430-434, (2006).
Nagel et al., Some Experiments on Freezedrying of Inactivated Poliomyelitis-Vaccines, Archives of Virology, 12: 718-720 (Nov. 14, 1962).
Galazka (ed.), Temperature sensitivity of vaccines, WHO/IVB//06. 10 pp. 33-38 (Aug. 2006).
Data Sheet for Infanrix™ -IPV+Hib ("http://www.medsafe.govt.nz/profs/datasheet/i/InfanrixIPVHibinj.htm" on Jun. 4, 2011), submitted in Opposition file history of EP1575612 (European equivalent to U.S. Appl. No. 10/533,464).
Declaration of Yves Mayeresse dated Apr. 22, 2010, submitted in Opposition file history of EP1575612 (European equivalent to U.S. Appl. No. 10/533,464).
Definition of "CONSTITUENT" ("http://dictionary.reference.com/browse/constituent" on Jul. 4, 2011), submitted in Opposition file history of EP1575612 (European equivalent to U.S. Appl. No. 10/533,464).
Decision in Opposition of EP1575612 (European equivalent to U.S. Appl. No. 10/533,464) dated Jul. 1, 2010.
Grounds for Decision in Opposition of EP1575612 (European equivalent to U.S. Appl. No. 10/533,464) dated Jul. 20, 2010.
Hekker,"Freeze drying of inactivated poliomyelitis vaccine, IXTH Eur. Symp." (1963), European, Supp. Poliomyelitis, Allied Disbases, Stockholm, pp. 335-340.
Barrington, T et al.,"Opposite effects of actively and passively acquired immunity to the carrier on responses of human infants to a Haemophilus influenzae type b conjugate vaccine", (1994), Infection and Immunity, vol. 62, No. 1; pp.9-14.
Claesson B A et al., "Clinical and immunologic responses to the capsular polysaccharide of Haemophilus influenzae type b alone or conjugated to tetanus toxoid in 18 - to 23 month old children", (1988), The Journal of Pediatrics, vol. 112; pp. 695-702.
Nagel, J, et al., "Some Experiments on freezedrying of inactivated Poliomyelitis Vaccines", (1962), National Institute of Public Health.
Begue, et al., "Vaccines haemophilus influenzae", (1993), Bulletin de l'academine Nationale de Medicine, vol. 177; pp. 1381-1390.
Singer, C., et al., "Quantitation of poliovirus antigens in inactivated viral vaccines by Enzyme-Linked Immunosorbent Assay Using Animal Sera and Monoclonal Antibodies", (1989), Journal of Biological Standardization, vol. 17, pp. 137-150.
Frasch,"Haemophilus influenzae type b conjugate and combination vaccines" (1995). Clinical Immunotherapeutics, vol. 4, No. 5, pp. 376-386.
Sawyer, L.A. et al.,"Potency of Wild-Type or Sabin Trivalent Inactivated Poliovirus Vaccine, by Enzyme-Linked Assay using Monoclonal Antibodies Specific for each antigenic Site", (1997), Biologicals, vol. 25, pp. 299-306.
Ho, M M et al.,"Assessment of the stability and immunogenicity of meningococcal oligosaccharide C-CRM197 conjugates vaccines", (2001), Vaccine, vol. 19, pp. 716-725.
Barrington, et al., "Non-epitope specific suppression of the antibody response to Haemophilus influenzae type b conjugate vaccines by preimmunization with vaccine components", (1993), Infections and Immunity, vol. 61, No. 2; pp. 432-438.
Corbel, M J; "Control testing of combined vaccines: a consideration of potential problems and approches", (1994) Biologicals, vol. 22; pp. 353-360.

* cited by examiner

A

B

C

D

IMMUNOGENIC COMPOSITION

This application is a 371 of International Application No. PCT/EP2003/012160, filed 30 Oct. 2003.

The present invention relates to immunogenic compositions comprising a dried solid or high viscosity liquid formulation of inactivated polio virus (IPV) which retains immunogenicity. The invention also includes a vaccine comprising a dried solid or high viscosity liquid formulation of IPV. A further aspect of the invention is a process for preserving inactivated polio virus (IPV) as a dried solid or high viscosity liquid. This process comprises preparing a sample by suspending or dissolving IPV and a bacterial polysaccharide in a solution of a stabilising agent and subjecting the sample to temperature and pressure conditions which result in solvent being lost from the sample. Pressure and temperature conditions are maintained or adjusted so that solvent is removed and the sample dries to form a solid or high viscosity liquid. Such formulations may be reconstituted prior to use or used directly.

IPV is well known as a component of vaccines, however, it is formulated as a liquid, for example in Infanrix Penta®. The process of freeze-drying IPV has been associated with the loss of antigenicity so that it is difficult to formulate an effective vaccine comprising a dried form of IPV. Dried vaccine formulations are known, particularly in the case of bacterial polysaccharides. The PRP polysaccharide of *Haemophilus influenzae* b (Hib) is frequently formulated as a dried solid, for example in Infanrix Hexa®(WO99/48525).

There are several reasons why a dried formulation of IPV would be advantageous. Dried formulations have good storage properties and can increase the shelf life of a vaccine containing IPV. The possibility of drying IPV also makes IPV a more flexible vaccine constituent and enables it to be formulated in new combination vaccines which were not previously possible. Some vaccines contain liquid and dried solid components which are mixed just prior to administration (for example Infanrix Hexa®). Infanrix Hexa contains a dried Hib component which is reconstituted with DTPa-HepB-IPV just prior to use. By formulating IPV together with Hib as a dried solid, it would be possible to add further components to the liquid part of the vaccine, which might otherwise be incompatible with IPV.

Several techniques for drying vaccine components are known in the art. Traditionally, this has been accomplished using the process of freeze drying in which a solution of the substance is made and the sample is frozen. During the primary drying phase, most of the water is removed by sublimation from ice under reduced pressure conditions and a porous 'cake' is formed. This is usually followed by a secondary drying phase when the pressure and temperature are changed and water is evaporated from the solid 'cake'. The resulting lyophilised sample has improved stability compared to a liquid formulation. However, the freeze drying process is lengthy and can be the rate limiting step in a production process.

Product variability is also a problem when many samples are being batch lyophilised in a large dryer unit. The conditions on the shelves of the freeze dryer vary between different positions leading to samples lyophilising at different rates under different conditions. For certain biological materials such as live virus, there can be significant loss of activity during the freeze drying process (Pikal (1994) ACS Symposium 567: 120-133). Many freeze dried substances are still unstable at ambient temperature (Carpenter et al (1994) ACS Symposium 567; 134-147).

Damage caused by the process of freezing may be circumvented to some degree by the use of cryoprotectants such as polyols. Further improvements on the process of lyophilisation have also been made by avoiding freezing the sample during the process and removing water by boiling (WO96/40077; U.S. Pat. No. 6,306,345). This method involves preparing a mixture of a glass-matrix forming material in a suitable solvent together with the sample to be preserved, evaporating bulk solvent from the mixture to obtain a syrup, exposing the syrup to a pressure and temperature sufficient to cause boiling of the syrup and removing residual solvent.

A similar method was described in U.S. Pat. No. 5,766,520, in which the process involves partially removing the water to form a viscous fluid and further subjecting the syrup to vacuum to cause it to 'boil' and further drying at temperatures substantially lower than 100° C. This method still suffers from some of the problems of conventional freeze-drying. When the process is carried out in a large freeze-dryer, samples will dry at different rates depending on their position on the shelf and this leads to different samples loosing different amount of activity during the drying process. This leads to a lack of consistency within a batch.

To date, no successful example of making a dried solid vaccine formulation of IPV that retains a high degree of antigenicity and/or immunogenicity has been reported.

Accordingly, the present invention discloses an immunogenic composition comprising IPV and a stabilising agent, formulated as a dried composition or highly viscous liquid, which after reconstitution is capable of generating an immune response against polio virus. The presence of a stabilising agent is crucial to the preservation of antigens and polyols are shown to be effective. IPV is preferably dried in the presence of a bacterial polysaccharide which leads to retention of a higher percentage of the original antigens in terms of antigenicity and/or immunogenicity. The present invention encompasses methods of preserving a composition comprising IPV, preferably in the presence of a polyol and a bacterial polysaccharide, wherein the antigenicity and/or immunogenicity of IPV is retained. Lyophilisation of IPV in the presence of polysaccharides leads to an improvement in antigen retention for IPV compared to lyophilisation of IPV alone. In addition, the immunogenicity of Hib is also enhanced by being formulated together with IPV as a dried solid or highly viscous liquid. In particular, when reconstituted extemporaneously with liquid DTP vaccines (described below), the inventors have found that Hib titres are not as reduced by the aluminum hydroxide component of the DTP vaccine as would have been the case without the presence of IPV.

The method of drying used can also influence the antigenicity and/or immunogenicity retention of IPV. A foam drying process for drying IPV was more effective at retaining antigenicity of IPV than conventional freeze drying techniques. Surprisingly, the inclusion of a freezing step in the foam drying process did not lead to loss of antigenicity but rather led to the development of a quick and effective preservation process. A further preferred method of the invention retains high levels of IPV antigenicity and/or immunogenicity by drying the sample containing IPV without freezing or foam formation, resulting in the formation of a dried formulation, preferably a highly viscous liquid formulation.

The invention provides a dried formulation of IPV which will have benefits of storage stability. The dried formulation can be reconstituted quickly and easily just prior to administration. Where the preferred foam drying process is used, the foamed cake is particularly easily reconstituted due to the greater surface area of the cake.

Additional benefits of a dried solid or highly viscous liquid formulation of IPV and Hib include enhanced immunogenicity of the Hib component. It is well known that in multicomponent vaccines, other parts of the vaccine formulation can lead to interference with Hib immunogenicity (WO96/40242, WO97/00697). The inclusion of IPV in a dried formulation with Hib can reduce this problem, especially if the dried IPV-Hib composition is mixed with diphtheria, tetanus and pertussis components prior to administration.

Although lyophilisation of IPV in the presence of a bacterial polysaccharide is possible using a conventional freeze drying approach, it is preferred to use a foam drying technique or a gentle drying process which does not involve freezing or foam formation. These processes result in even greater antigenicity and/or immunogenicity retention in IPV and the resultant cake is also easier and quicker to reconstitute. The processes also have advantages in being quicker and more energy efficient than standard freeze-drying techniques. Since the lyophilisation step is often the rate limiting step in vaccine production, the use of the preferred processes would result in higher levels of vaccine production without additional investment in plant. The introduction of a freezing step into the preferred foam drying process also leads to improved batch reproducibility.

A—Shows the appearance of the preservation samples as inserted into the freeze drying as a liquid formulation.

B—Shows the appearance of the preservation samples as the pressure is reduced to 1.5 mbars. The samples begin to freeze at slightly different rates due to differing conditions in each vial.

C—Shows the appearance of the preservation samples at 0.1 mbars, where all samples have become completely frozen.

D—Shows the appearance of the preservation samples as the pressure is increased to 0.8-3.5 mbars. A foamed glass is formed as the preservation sample foams and solvent evaporates.

Figure 2:

FIG. 2—Photograph of the highly viscous liquid in inverted vials.

DETAILED DESCRIPTION

Immunogenic Compositions of the Invention

The invention includes immunogenic compositions, formulated as a dried solid or a highly viscous liquid comprising IPV and a stabilising agent, in which the antigenicity and/or immunogenicity of IPV is retained following reconstitution. The dried solid or highly viscous liquid formulation of IPV is capable of generating an immune response, preferably a protective immune response, against polio virus, preferably after reconstitution and inoculation.

IPV is defined as inactivated polio virus (preferably comprising types 1, 2 and 3 as is standard in the vaccine art, most preferably the Salk polio vaccine). A vaccine dose of IPV contains 20-80, preferably 40 or 80 D-antigen units of type 1 Mahoney), 4-16, preferably 8 or 16 D-antigen units of type 2 (MEF-1) and 20-64, preferably 32 or 64 D-antigen units of type 3 (Saukett).

When dried by a method of the invention, preferably the antigenicity of 1, 2, or all 3 of types 1, 2 and 3 of polio virus are retained; more preferably the antigenicity of type 1; type 2; type 3; type 1 and type 2; type 1 and type 3; type 2 and type 3; or type 1, type 2 and type 3 is retained at a level of at least 40%, 50%, 60%, 70%, 80%, 90%, 95% or 98% of the antigenicity of a reference sample which has not been subjected to the drying process. This can be measured, following reconstitution of the dried solid or highly viscous liquid in an aqueous solution, by any suitable method including by ELISA using polyclonal and/or monoclonal antibodies against polio virus type 1, 2 and/or 3.

When dried by a method of the invention, preferably the immunogenicity of 1, 2, or all 3 of types 1, 2 and 3 of polio virus are retained; more preferably the immunogenicity of type 1; type 2; type 3; type 1 and type 2; type 1 and type 3; type 2 and type 3; or type 1, type 2 and type 3 is retained at a level of at least 40%, 50%, 60%, 70%, 80%, 90%, 95% or 98% of the immunogencity of a reference sample which has not been subjected to the drying process. This can be measured, following reconstitution of the dried solid or highly viscous liquid in an aqueous solution, by any suitable method. In a preferred method, the dried formulation is reconstituted in an aqueous solution and is inoculated into an animal, preferably a rat. After a suitable period of time, antisera are collected from the inoculated animals and seroconversion is tested. Preferably, a relative potency of at least 0.4, 0.5, 0.6, 0.7, 0.8 or 0.9 is achieved, compared to an undried reference sample.

A dried solid composition is a formulation which has had solvent removed by a process of lyophilisation, sublimation, evaporation or desiccation so that less than or equal to 15%, 12%, 10%, 7%, 5%, 4%, preferably 3%, 2% or most preferably 1%. solvent remains. The term 'dried solid' comprises glasses, rubbers or crystalline solids with a solid appearance. Any of the methods described above can be used to make such a dried solid. Solvent is removed by sublimation, boiling or evaporation, preferably by evaporation.

A highly viscous liquid is defined as a material with a solvent content less than or equal to 15, 12, 10, preferably 8, 5, 4, 3, 2 or 1%. The highly viscous liquid has a sufficiently low solvent content such that the active agent is preserved in a stable state for at least 3,6,9,12 or 24 months at 4° C., allowing the active agent to retain at least 40, 50, 60, preferably 70, 80, 90, 95% of its antigenicity and/or immunogencity over this period. The highly viscous liquid has not been exposed to the formations of bubbles that is involved in foam formation. Preferably, the highly viscous liquid has a solid appearance but is a glass and is able to flow very slowly over a period of days, preferably weeks, more preferably months.

Immunogenic compositions of the invention are formulated as a dried solid or highly viscous liquid comprising IPV and a stabilising agent and preferably a bacterial polysaccharide. The stabilising agent is any of the compositions described below. The bacterial polysaccharide comprises capsular polysaccharides derived from any bacterium, preferably one or more of *Neisseria meningitidis, Haemophilus influenzae* b, *Streptococcus pneumoniae*, Group A Streptococci, Group B Streptococci, *Staphylococcus aureus* or *Staphylococcus epidermidis*.

Preferably the PRP capsular polysaccharide of *Haemophilus influenzae* b is present as a dried solid or highly viscous liquid. In a further preferred embodiment, the immunogenic composition comprises dried solid or highly viscous liquid formulations of capsular polysaccharides derived from one or more of serogroups A, C, W-135 and Y of *Neisseria meningitidis* (meningococcal polysaccharides). A further preferred embodiment comprises dried solid or highly viscous liquid formulations of capsular polysaccharides derived from *Streptococcus pneumoniae*. The pneumococcal capsular polysaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F). A further preferred embodiment contains the Type 5, Type 8 or 336 capsular polysaccharides of *Staphylococcus aureus*. A further preferred embodiment contains the Type I, Type II or Type III capsular polysaccharides of *Staphylococcus epidermidis*. A further preferred embodiment contains the Type Ia, Type Ic, Type II or Type III capsular polysaccharides of Group B *streptocoocus*. A further preferred embodiment contains the capsular polysaccharides of Group A *streptococcus*, preferably further comprising at least one M protein and more preferably multiple types of M protein.

In one embodiment of the invention, the bacterial polysaccharides are full length, being purified native polysaccharides. In an alternative embodiment of the invention, the polysaccharides are sized between 2 and 20 times, preferably 2-5 times, 5-10 times, 10-15 times or 15-20 times, so that the polysaccharides are smaller in size for greater manageability. Oligosaccharides are used in a preferred embodiment. Oligosaccharides typically contain between 2 and 20 repeat units.

The invention further includes immunogenic compositions comprising more than one bacterial polysaccharide and IPV as a dried solid or highly viscous liquid. Preferably, IPV is combined with one or more of Hib (*Haemophilus influenzae* type b) PRP polysaccharide and/or meningococcal A, C, W and/or Y polysaccharides and/or pneumococcal polysaccharides. Most preferably the active agents comprise, IPV and Hib; IPV and MenC; IPV and Hib and MenC; IPV and MenA and C; IPV and Hib and Men A and C; IPV and Hib and Men A and C and Y; or IPV and Hib and Men C and Y.

The above particularised active agents may also comprise one or more pneumococcal capsular polysaccharides as described below.

In the above compositions where polysaccharides are used, oligosaccharides may also be employed (as defined above).

Although these compositions may be adjuvanted (as described below), they are preferably unadjuvanted or preferably do not comprise aluminium salts.

Preferably the polysaccharides or oligosaccharides are conjugated to a peptide or carrier protein comprising T-helper epitopes (as described below).

Capsular polysaccharides present in immunogenic compositions of the invention are unconjugated or conjugated to a carrier protein such as tetanus toxoid, tetanus toxoid fragment C, diphtheria toxoid, CRM197, pneumolysin, Protein D (U.S. Pat. No. 6,342,224). Tetanus toxin, diphtheria toxin and pneumolysin are detoxified either by genetic mutation and/or preferably by chemical treatment. A preferred embodiment of the invention has Hib conjugated to tetanus toxoid.

Where more than one conjugated polysaccharide is present in the immunogenic composition of the invention, the polysaccharides are conjugated to the same carrier protein or to different carrier proteins. Preferred embodiments of the invention contain meningococcal polysaccharides conjugated to a carrier protein. Where conjugated Hib and meningococcal polysaccharides are present, they are conjugated to the same carrier protein or to different carrier proteins.

The polysaccharide conjugate may be prepared by any known coupling technique. In a preferred coupling technique, the polysaccharide is coupled via a thioether linkage. This conjugation method relies on activation of the polysaccharide with 1-cyano-4-dimethylamino pyridinium tetrafluoroborate (CDAP) to form a cyanate ester. The activated polysaccharide may thus be coupled directly or via a spacer group to an amino group on the carrier protein. Preferably, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 Uniformed Services University.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide activated polysaccharide derivatised with adipic acid hydrazide (ADH) to the protein carrier by Carbodiimide condensation (Chu C. et al Infect. Immunity, 1983 245 256).

Polysaccharides which are incorporated as part of the immunogenic composition of the invention may be unabsorbed or absorbed onto an adjuvant, preferably an aluminium salt (aluminium phosphate or aluminium hydroxide), most preferably aluminium phosphate.

Immunogenic compositions of the invention comprise a stabilising agent which can help to prevent damage during the desiccation process. Any of the stabilising agent described below, including glass forming polyols can be incorporated into the immunogenic composition, whether as a dried solid, a foamed glass or a highly viscous liquid composition using the processes of the invention. Preferred stabilising agents include sucrose, sorbitol, lactose and trehalose.

The preferred combinations, dried by the processes of the invention may be combined with other antigens in a combination vaccine which are desiccated or liquid formulations which are used to reconstitute the dried components.

Additional Components

Dried solid or highly viscous liquid formulations of the invention incorporating IPV and a stabilising agent may additionally be formulated with further vaccine components. A preferred vaccine contains a dried solid or highly viscous liquid formulation of IPV and a bacterial polysaccharide which may be mixed with a liquid formulation comprising additional vaccine components. After reconstitution of the solid components with the liquid components, the complete vaccine is administered by injection.

The additional components include capsular polysaccharides derived from one or more of *Neisseria meningitidis*, *Streptococcus pneumoniae*, Group A Streptococci, Group B Streptococci, *Staphylococcus aureus* or *Staphylococcus epidermidis*. In a preferred embodiment, the immunogenic composition comprises capsular polysaccharides derived from one or more of serogroups A, C, W-135 and Y of *Neisseria meningitidis*. A further preferred embodiment comprises capsular polysaccharides derived from *Streptococcus pneumoniae*. The pneumococcal capsular polysaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F). A further preferred embodiment contains the Type 5, Type 8 or 336 capsular polysaccharides of *Staphylococcus aureus*. A further preferred embodiment contains the Type I, Type II or Type III capsular polysaccharides of *Staphylococcus epidermidis*. A further preferred embodiment contains the Type Ia, Type Ic, Type II or Type III capsular polysaccharides of Group B *streptocoocus*. A further preferred embodiment would contain the capsular polysaccharides of Group A streptococcus, preferably further comprising at least one M protein and more preferably multiple types of M protein.

The immunogenic composition of the invention may be formulated with protein antigens. Preferred pneumococcal proteins antigens are those pneumococcal proteins which are exposed on the outer surface of the *pneumococcus* (capable of being recognised by a host's immune system during at least part of the life cycle of the *pneumococcus*), or are proteins which are secreted or released by the *pneumococcus*. Most preferably, the protein is a toxin, adhesin, 2-component signal tranducer, or lipoprotein of *Streptococcus pneumoniae*, or fragments thereof. Particularly preferred proteins include, but are not limited to: pneumolysin (preferably detoxified by chemical treatment or mutation) [Mitchell et al. Nucleic Acids Res. 1990 Jul. 11; 18(13): 4010 "Comparison of pneumolysin genes and proteins from *Streptococcus pneumoniae* types 1 and 2.", Mitchell et al. Biochim Biophys Acta 1989 Jan. 23; 1007(1): 67-72 "Expression of the pneumolysin gene in *Escherichia coli*: rapid purification and biological properties.", WO 96/05859 (A. Cyanamid), WO 90/06951 (Paton et al), WO 99/03884 (NAVA)]; PspA and transmembrane deletion variants thereof (U.S. Pat. No. 5,804,193—Briles et al.); PspC and transmembrane deletion variants thereof (WO 97/09994—Briles et al); PsaA and transmembrane deletion variants thereof (Berry & Paton, Infect Immun 1996 Dec.; 64(12):5255-62 "Sequence heterogeneity of PsaA, a 37-kilodalton putative adhesin essential for virulence of *Streptococcus pneumoniae*"); pneumococcal choline binding proteins and transmembrane deletion variants thereof; CbpA and transmembrane deletion variants thereof (WO 97/41151; WO 99/51266); Glyceraldehyde-3-phosphate-dehydrogenase (Infect. Immun. 1996 64:3544); HSP70 (WO 96/40928); PcpA (Sanchez-Beato et al. *FEMS Microbiol Lett* 1998, 164: 207-14); M like protein, (EP 0837130) and adhesin 18627, (EP 0834568). Further preferred pneumococcal protein antigens are those disclosed in WO 98/18931, particularly those selected in WO 98/18930 and PCT/US99/30390.

Preferred Neisserial proteins to be formulated with the immunogenic composition of the invention include ThpA (WO93/06861; EP586266; WO92/03467; U.S. Pat. No. 5,912,336), TbpB (WO93/06861; EP586266), Hsf (WO99/31132), NspA (WO96/29412), Hap (PCT/EP99/02766), PorA, PorB, OMP85 (also known as D15) (WO00/23595), PilQ (PCT/EP99/03603), PldA (PCT/EP99/06718), FrpB (WO96/31618 see SEQ ID NO:38), FrpA or FrpC or a conserved portion in common to both of at least 30, 50, 100, 500, 750 amino acids (WO92/01460), LbpA and/or LbpB (PCT/EP98/05117; Schryvers et al Med. Microbiol. 1999 32: 1117), FhaB (WO98/02547), HasR (PCT/EP99/05989), lipo02 (PCT/EP99/08315), MltA (WO99/57280) and ctrA (PCT/EP00/00135). Neisserial protein may be added as purified proteins or as part of an outer membrane vesicle preparation.

The immunogenic composition is preferably formulated with antigens providing protection against one or more of Diphtheria, tetanus and *Bordetella pertussis* infections. The pertussis component may be killed whole cell *B. pertussis* (Pw) or is preferably a cellular pertussis (Pa) which contains at least one antigen (preferably two or all three) from PT, FHA and 69 kDa pertactin certain other a cellular vaccines also contain agglutinates, such as Film 2 and Film 3 and these vaccines are also contemplated for use in the invention. Typically, the antigens providing protection against Diphtheria and Tetanus are Diphtheria toxoid and tetanus toxoid. The toxoids are chemically inactivated toxins, for example following treatment with formaldehyde, or toxins inactivated by the introduction of one or more point mutations.

Alternatively the immunogenic composition of the invention may be provided as a kit with the dried solid, foamed glass or highly viscous liquid in one container and liquid DTPa or DTPw in another container. Such kits can for example, comprise a dual chamber syringe with the dried and liquid components contained in the same syringe but in different chambers. The dried component is then reconstituted with the liquid vaccine immediately prior to injection as a single vaccine. Thus for example, the dried solid, foamed glass or highly viscous liquid of the invention is reconstituted with the liquid DTPa or DTPw vaccine (preferably extemporaneously) and administered as a single vaccine. The DTPa or DTPw vaccine typically is adjuvanted at least in part with an aluminium salt, such as aluminium phosphate and/or aluminium hydroxide (for instance Infanrix® and Tritanrix® vaccines of GlaxoSmithKline Biologicals s.a.).

The immunogenic composition is optionally formulated with one or more antigens that can protect a host against non-typeable *Haemophilus influenzae*, RSV and/or one or more antigens that can protect a host against influenza virus. Preferred non-typeable *H. influenzae* protein antigens include Fimbrin protein (U.S. Pat. No. 5,766,608) and fusions comprising peptides therefrom (eg LB1 Fusion) (U.S. Pat. No. 5,843,464—Ohio State Research Foundation), OMP26, P6, protein D, ThpA, TbpB, Hia, Hmw1, Hmw2, Hap, and D15.

Preferred influenza virus antigens include whole, live or inactivated virus, split influenza virus, grown in eggs or MDCK cells, or Vero cells or whole flu virosomes (as described by R. Gluck, Vaccine, 1992, 10, 915-920) or purified or recombinant proteins thereof, such as HA, NP, NA, or M proteins, or combinations thereof.

Preferred RSV (Respiratory Syncytial Virus) antigens include the F glycoprotein, the G glycoprotein, the HN protein, the M protein or derivatives thereof.

Combination vaccines comprising DTP-Hib are known in the art. However there are problems associated with certain formulations which involve simple mixing of Hib with other antigens. Unless carefully formulation, the antibody titres raised against the Hib component can be lower than those elicited by the same dose of Hib inoculated separately, due to interference with other components of the vaccine. Although this problem is well known in the art and has been addressed in various ways, the immunogenic compositions of the invention in which Hib and IPV are formulated together as a dried solid or highly viscous liquid provides an alternative solution to this problem.

The immunogenic compositions of the invention may form part of a vaccine kit in which IPV and Hib are present in one component of the kit and further components, as described above, are present in a second component, for example, a dual chamber syringe as described herein. The two components are mixed together just before administration of the vaccine. In such formulations, the component comprising IPV and Hib is preferably a dried solid, foamed glass or highly viscous liquid, although it is optionally formulated as a liquid. This formulation results in antibody titres against the Hib component being clinically acceptable to provide protection against the *Haemophilus influenzae* b pathogen. Typically, the antibody titre in the combination vaccine are at least 85%, 90%, preferably about 100% or more of those elicited by the same dose of Hib in a monovalent Hib vaccine.

Vaccines of the Invention

The immunogenic compositions of the invention described above are preferably formulated as a vaccine. Preferably, the vaccine contains an amount of an adjuvant sufficient to enhance the immune response to the immunogen. Suitable adjuvants include, but are not limited to, aluminium salts such as aluminium hydroxide and aluminium phosphate, squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polphosphazene and derivatives, and immunostimulating complexes (ISCOMs) such as those described by Takahashi et al. (1990) Nature 344:873-875. For veterinary use and for production of antibodies in animals, mitogenic components of Freund's adjuvant can be used.

The vaccine formulations of the invention are preferably reconstituted prior to use. Reconstitution involves the mixing of a liquid component of the vaccine with the dried solid, foamed glass or highly viscous liquid formulation of the invention. The invention also encompasses a container with a water repellent internal surface containing the immunogenic composition or vaccine of the invention. The use of such a container is advantageous because it leads to the dried composition sitting at the bottom of the tube in a form in which it is more easy to reconstitute.

It is advantageous to incorporate a coloured dye into the preservation sample in order to allow easier visualisation of the dried composition of the invention. This is particularly important during reconstitution to ensure that the dried solid or highly viscous liquid is thoroughly reconstituted prior to use. Preferably, the coloured dye maintains its colour at a neutral pH and is compatible with injection into a patient. Most preferably the coloured dye is phenol red.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunising dosages to be adminstered. Such factors are known in the vaccine art and it is well within the skill of immunologists to make such determinations without undue experimentation.

The substance can be present in varying concentrations in the immunogenic composition of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is preferably one which will provide a single therapeutically effective dosage. Super-saturated solutions can also be used if a foamed glass is formed prior to crystallisation. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application Generally, it is expected that each dose will comprise 1-100 ug of protein antigen, preferably 5-50 ug and most preferably 5-25 ug. Preferred doses of bacterial polysaccharides are 10-20 ug, 10-5 ug, 5-2.5 ug or 2.5-1 ug. The preferred amount of the substance varies from substance to substance but is easily determinable by one of skill in the art.

Methods of the Invention

The methods of the invention are for preserving a composition comprising IPV and a stabilising agent, resulting in a composition in which the antigenicity of IPV is retained. Preferably, a bacterial polysaccharide is incorporated in the sample to be dried.

In one embodiment, the method of the invention involves drying IPV and comprises the steps of:
preparing a preservation sample by suspending or dissolving IPV in a solution of a stabilising agent; preferably a bacterial polysaccharide and/or a glass forming polyol are present in the preservation sample;
subjecting the preservation sample to such temperature and pressure conditions that solvent is lost from the preservation sample; and
removing solvent until the preservation sample dries to form a solid or highly viscous liquid in which the antigenicity and/or immunogenicity of IPV is retained.

In a preferred embodiment, the preservation sample is inserted into a container with a water repellent interior prior to drying.

A further method of the invention involves foam drying, comprising the steps of:
preparing a preservation sample by suspending or dissolving IPV in a solution of a stabilising agent; preferably a bacterial polysaccharide and/or a glass forming polyol are present in the preservation sample;
subjecting the preservation sample to such temperature and pressure conditions that the preservation sample forms a foam; and
removing solvent until the foam dries to form a solid in which the antigenicity and/or immunogenicity of IPV is retained.

A preferred foam drying method of the invention uses a container with a water repellent interior surface and contains the steps of:
preparing a preservation sample by suspending or dissolving IPV and preferably a bacterial polysaccharide in a solution of a stabilising agent;
inserting the preservation sample into a container with a water repellent interior surface;
subjecting the container containing the preservation sample to such temperature and pressure conditions so that the preservation sample forms a foam;
removing solvent until the foam dries to form a solid in which the antigenicity and/or immunogenicity of IPV is retained.

The foam drying methods of the invention described above optionally comprise a freezing step. The preservation sample may be wholly or partially frozen. Therefore some methods of the invention comprise the steps of:
preparing an at least partially frozen preservation sample by suspending or dissolving IPV and preferably a bacterial polysaccharide in a solution of a stabilising agent and freezing the mixture;
subjecting the at least partially frozen preservation sample to such temperature and pressure conditions that the preservation sample forms a foam; and
removing solvent until the foam dries to form a solid in which the antigenicity and/or immunogenicity of IPV is retained.

The freezing step of the above method is preferably by the process of quench freezing in which reduction of pressure is the cause of freezing by evaporation. This causes rapid freezing of the sample which leads to less antigen loss. Therefore a process of the invention includes the steps of:
preparing a preservation sample by suspending or dissolving IPV and preferably a bacterial polysaccharide in a solution of a stabilising agent;
subjecting the preservation sample to reduced pressure such that the preservation sample becomes at least partially frozen;
subjecting the at least partially frozen preservation sample to such temperature and pressure conditions that the preservation sample forms a foam; and
removing solvent until the foam dries to form a solid in which the antigenicity and/or immunogenicity of IPV is retained.

A further preferred method of the invention is used for preserving IPV and comprises the steps of:
- preparing a preservation sample by suspending or dissolving IPV in a solution of a stabilising agent;
- subjecting the preservation sample to such temperature and pressure conditions that the preservation sample looses solvent by evaporation, without bubbling to form a foam and preferably without freezing;
- removing solvent until the sample dries to form a highly viscous liquid in which and antigencity and/or immunogenicity of IPV is retained.

The methods of the invention produce a formulation of IPV that is able to withstand extended storage during which the antigenicity and/or immunogenicity of IPV is maintained. Preferably the IPV retains at least 40, 50, 60, 70, preferably 80, 90, 95% of its original antigenicity and/or immunogenicity over a period of at least 3, 6, 9, 12, 24 months storage at 4° C. Antigenicity and immunogenicity are measured after reconstitution of IPV in a suitable aqueous solution, and using a suitable method, for instance those described above.

The method of drying without freezing or foam formation is particularly applicable for use where the active agents to be dried are prone to loss of activity and/or antigenicity during the drying process due to exposure to freezing or the bubbling associated with foam formation. It is also particularly applicable for use where a lower concentration of the glass forming polyol is advantageous and/or where a shorter drying process is preferred.

Stabilising Agent

The stabilising agent to be used in the methods of the invention will preferably comprise glass forming polyols. Suitable materials include, but are not limited to, all polyols, including carbohydrate and non-carbohydrate polyols. Preferably the stabilising polyol enables the active agent to be stored without substantial loss of activity by denaturation, aggregation or other means. Particularly suitable materials include sugars, sugar alcohols and carbohydrate derivatives. Preferably, the glass forming polyol is a carbohydrate or derivatives thereof, including glucose, maltulose, iso-maltulose, lactulose, sucrose, maltose, lactose, iso-maltose, maltitol, lactitol, palatinit, trehalose, raffinose, stachyose, melezitose or dextran, most preferably trehalose, sucrose, sorbitol, raffinose, mannitol, lactose, lactitol or palatinit.

Bacterial polysaccharides act as a stabilising agent and preferred embodiments of the invention incorporate bacterial polysaccharides as a constituent of the stabilising agent. The bacterial polysaccharide plays a dual role of stabilising agent and immunogen in this embodiment.

Carbohydrates include, but are not limited to, monosaccharides, disaccharides, trisaccharides, oligosaccharides and their corresponding sugar alcohols, polyhydroxyl compounds such as carbohydrate derivatives and chemically modified carbohydrates, hydroxyethyl starch and sugar copolymers. Both natural and synthetic carbohydrates are suitable for use. Synthetic carbohydrates include, but are not limited to, those which have the glycosidic bond replaced by a thiol or carbon bond. Both D and L forms of the carbohydrates may be used. The carbohydrate may be non-reducing or reducing. Where a reducing carbohydrate is used, the addition of inhibitors of the Maillard reaction is preferred.

Reducing carbohydrates suitable for use in the invention are those known in the art and include, but are not limited to, glucose, maltose, lactose, fructose, galactoase, mannose, maltulose and lactulose. Non-reducing carbohydrates include, but are not limited to, non-reducing glycosides of polyhydroxyl compounds selected from sugar alcohols and other straight chain polyalcohols. Other useful carbohydrates include raffinose, stachyose, melezitose, dextran, sucrose, cellibiose, mannobiose and sugar alcohols. The sugar alcohol glycosides are preferably monoglycosides, in particular the compounds obtained by reduction of disaccharides such as lactose, maltose, lactulose and maltulose.

Particularly preferred carbohydrates are trehalose, sucrose, sorbitol, maltitol, lactitol, palatinit and glucopyranosyl-1→6-mannitol.

Amino acids can act as stabilising agents and can be used by themselves and preferably in combination with a polyol. Preferred amino acids include glycine, alanine, arginine, lysine and glutamine although any amino acid, or a combination of amino acids, peptide, hydrolysed proteins or protein such as serum albumin can act as a stabilising agent.

Preferably, the preservation sample will contain a component capable of inhibiting crystal formation in the dried solid or highly viscous liquid of the invention. Salts and other molecules including amino acids and phenol red inhibit crystal formation.

The concentration of the stabilising agent used in the process of the invention may be between 1% and 50% weight/volume, preferably 1-5%, 5-10%, 5-10%, 15-20%, 20-25% or 25-50%, most preferably less than 25% (w/v). The amounts of stabilising agent required is proportional to the amount of salts present. Therefore, although levels of stabilising agent between 3% and 10% are preferred, higher concentrations of 10% to 25% (w/v) may be required to dry samples with a high salt content.

Container

Different mixtures and various container shapes and sizes can be processed simultaneously. Ideally, the container size used is sufficient to contain the initial mixture and accommodate the volume of the dried formulation formed thereof. Typically, this is determined by the mass of the glass forming material, the surface area of the container and the temperature and pressure conditions, which determine whether foaming occurs. The mass of glass forming material must be sufficient to give viscous syrup, optionally to be foamed which translates practically as a minimal mass per unit area of container surface. This ratio varies from mixture to mixture and container used, but is easily determined empirically by one skilled in the art by following the procedures set forth herein. Any such containers can be used including Wheaton moulded and tube-cut vials.

The processes of the invention preferably use containers with a water repellent interior surface. This is achieved through coating the interior surface with a hydrophobic composition, for instance by siliconisation. Siliconisation is achieved by processes that are well known to those skilled in the art. In one method, the container is siliconised by rising the interior of the container with an emulsion of silicone, followed by processing through an oven at high temperature, typically 350° C. Alternatively, the water repellent interior surface is achieved by the container being made of a water repellent composition.

The water repellent interior surface of the container makes foam formation more likely to occur and more reproducible. This allows lower polyol concentrations to be used in the preservation sample which in turn decreases the length of time necessary to dry the sample, reduces the effect of Maillard reactions or other interactions with the polyol harming the active agent. Where the preservation samples comprises a vaccine, the resultant foamed glass is reconstituted quickly and easily due to the lower amount of polyol present and the resultant vaccine solution is less viscous, allowing easier administration. The water repellent interior surface allows easier reconstitution of the dried solid or highly viscous liquid since it encourages the sample to remain as at the bottom of the container so that it is easier to reconstitute effectively.

Although singular forms may be used herein, more than one stabilising agent, more than one additive, and more than one substance may be present. Effective amounts of these components are easily determined by one skilled in the art.

Solvent

The preservation sample is made by dissolving/suspending IPV and a stabilising agent in water to make an aqueous solution. Preferably, water is present in the preservation sample at a level of 5 to 98% by volume, more preferably 80-98% by volume, most preferably 85-98% by volume.

The volume of solvent can vary and will depend upon the stabilising agent and the substance to be incorporated as well as any additives. The minimum volume required is an amount necessary to solubilise the various components. However, homogeneously dispersed suspensions of the substance(s) can also be used. Suitable amounts of the components in specific embodiments are easily determinable by those skilled in the art in light of the examples provided herein.

Various additives can be put into the preservation sample. Typically, the additives enhance foam formation and/or the drying process and/or contribute to the solubilization of the substance. Alternatively, the additives contribute to the stability of the substance incorporated within the solid. One or more additives may be present.

As an example, addition of volatile/effervescent salts allows larger initial volumes and results in higher surface area within the foamed glass, thus effecting superior foam formation and more rapid drying. As used herein, volatile salts are salts which volatilise under the conditions used to produce a foamed glass. Examples of suitable volatile salts include, but are not limited to, ammonium acetate, ammonium bicarbonate and ammonium carbonate. Salts that decompose to give gaseous products also effect enhanced foam formation and more rapid drying. Examples of such salts are sodium bicarbonate and sodium metabisulphite. Preferably, the volatile salts are present in an amount of from about 0.01 to 5 M. Concentrations of up to 5 M are suitable for use herein. The resultant foamed glass has uniform foam conformation and is significantly drier compared to foamed glass in which volatile/effervescent salts are not used.

Another suitable additive is a foam stabilising agent, which can be used in combination with either the volatile or decomposing salt. This may either be a surface active component such as an amphipathic molecule (i.e. such as phospholipids and surfactants) or an agent to increase the viscosity of the foaming syrup, such as a thickening agent such as guar gum and their derivatives.

Another additive is an inhibitor of the Maillard reaction. Preferably, if the substance and/or glass matrix-forming material contains carbonyl and amino, imino or guanidino groups, the compositions further contain at least one physiologically acceptable inhibitor of the Maillard reaction in an amount effective to substantially prevent condensation of amino groups and reactive carbonyl groups in the composition. The inhibitor of the Maillard reaction can be any known in the art. The inhibitor is present in an amount sufficient to prevent, or substantially prevent, condensation of amino groups and reactive carbonyl groups. Typically, the amino groups are present on the substance and the carbonyl groups are present on the glass matrix forming material, or the converse. However, the amino acids and carbonyl groups may be intramolecular within either the substance or the carbohydrate.

Various classes of compounds are known to exhibit an inhibiting effect on the Maillard reaction and hence to be of use in the compositions described herein. These compounds are generally either competitive or non-competitive inhibitors of the Maillard reaction. Competitive inhibitors include, but are not limited to, amino acid residues (both D and L), combinations of amino acid residues and peptides. Particularly preferred are lysine, arginine, histidine and tryptophan. Lysine and arginine are the most effective. There are many known non-competitive inhibitors. These include, but are not limited to, aminoguanidine and derivatives and amphotericin B. EP-A-0 433 679 also describes suitable Maillard inhibitors which include 4-hydroxy-5,8-dioxoquinoline derivatives.

Active Agents

The methods of the invention are used to preserve inactivated polio virus (IPV—preferably comprising types 1, 2 and 3 as is standard in the vaccine art, most preferably the Salk polio vaccine). IPV contains 20-80, preferably 40 or 8-D-antigen units of type 1 (Mahoney), 4-20, preferably 8 or 16 D-antigen units of type 2 (MEF-1) and 20-64, preferably 32 or 64 D-antigen units of type 3 (Saukett). The IPV vaccine formulation is suitable for injection after reconstitution in an aqueous solution which preferably contains additional vaccine components.

The bacterial polysaccharide incorporated by the process of the invention are for example capsular polysaccharides derived from one or more of *Neisseria meningitidis, Haemophilus influenzae* b, *Streptococcus pneumoniae*, Group A Streptococci, Group B Streptococci, *Staphylococcus aureus* or *Staphylococcus epidermidis*, preferably the PRP capsular polysaccharides of *Haemophilus influenzae*. Preferred capsular polysaccharides also include those derived from one or more of serogroups A, C, W-135 and Y of *Neisseria meningitidis*. Further preferred capsular polysaccharides are derived from *Streptococcus pneumoniae*. The pneumococcal capsular polysaccharide antigens are preferably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most preferably from serotypes 1, 3, 4, 5, 6B, 7F, 9V, 14, 18C, 19F and 23F). A further preferred embodiment contains the Type 5, Type 8 or 336 capsular polysaccharides of *Staphylococcus aureus*. Further preferred polysaccharides include the Type I, Type II or Type III capsular polysaccharides of *Staphylococcus epidermidis*, the Type Ia, Type Ic, Type II or Type III capsular polysaccharides of Group B *streptocoocus*. Further preferred polysaccharides include the capsular polysaccharides of Group A *streptococcus*, preferably further comprising at least one M protein and more preferably multiple types of M protein.

Preferred combinations of active agents to be preserved using the processes of the invention comprise IPV. Preferably, IPV is combined with bacterial polysaccharides comprising one or more of Hib PRP polysaccharide and/or meningococcal A, C, W and/or Y polysaccharides and/or pneumococcal polysaccharides. Preferred combinations include IPV and Hib; IPV and MenC; IPV and MenA and C; IPV and Hib and Men C or IPV, Hib, Men A and C. Each bacterial polysaccharides may be present in doses of 1-5 μg, 5-10 μg, 10-20 μg or 20-40 μg.

Bacterial polysaccharides are unconjugated or conjugated to a carrier protein such as tetanus toxoid, tetanus toxoid fragment C, diphtheria toxoid, CRM197, pneumolysin or Protein D (U.S. Pat. No. 6,342,224).

The polysaccharide conjugate are prepared by any known coupling technique. A preferred conjugation method relies on activation of the polysaccharide with 1-cyano-4-dimethylamino pyridinium tetrafluoroborate (CDAP) to form a cyanate ester. The activated polysaccharide is coupled directly or via a spacer group to an amino group on the carrier protein.

Preferably, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 Uniformed Services University.

The conjugates are optionally prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide activated polysaccharide derivatised with adipic acid hydrazide (ADH) to the protein carrier by Carbodiimide condensation (Chu C. et al Infect. Immunity, 1983 245 256).

Drying Processes

In one embodiment the process of the invention involves drying IPV in the presence of a stabilising agent, preferably in the presence of a bacterial polysaccharide. In this process, the preservation sample is subjected to reduced temperature and pressure conditions. The temperature is reduced to less than 20° C. or 0° C., preferably less than −10° C. or −20° C., more preferably −40° C. or −60° C. The pressure is reduced to less than 1 mbar, preferably a pressure of, or less than 0.5, 0.1, more preferably 0.05 or 0.01 mbar. The reduced temperature and pressure conditions are maintained for at least 10, 12, 16, 20, preferably 24, 36, more preferably 48 or 72 hours. Solvent is removed until the preservation sample dries to form a solid.

Throughout this application, solid includes glasses, rubbers and crystals which form as the sample dries. Such solids preferably retain a water content of 10-20% or 5-10%, preferably 5-6%, 4-5%, or 3-4%, or 2-3%, more preferably 1-2% or 0-1% (w/w).

Foam Drying

A preferred process of the invention involves subjecting the preservation sample to such pressure and temperature conditions so that the sample begins to bubble, forming a foam.

The temperature within the preservation sample will be different from that external to the sample due to the endothermic nature of the evaporation process. References to temperature are to the conditions external to the preservation sample, for instance, where a large industrial freeze dryer is used, to the temperature of the shelf. This usually corresponds to the freeze dryer temperature setting.

A preferred embodiment of the invention achieves this by reducing the pressure while maintaining temperature conditions. The pressure is adjusted to at or below 8, 7, 6, preferably 5, 4, 3, more preferably 2, 1.5, 1, most preferably 0.8 or 0.5 mbar, while maintaining the temperature setting at a temperature above 0° C., preferably of between 10° C. to 15° C.; 15° C. to 20° C.; 20° C. to 25° C.; 25° C. to 30° C.; or 30° C. to 37° C. These conditions are maintained for at least 1, 2, 3, 4, 5, 8, 10, 12, 16 or 24 hours.

Another embodiment of the invention achieves foam formation by changing the temperature while maintaining reduced the pressure conditions. The temperature setting is increased to above 20° C., preferably to between 20° C. and 30° C.; 30° C. and 40° C.; 40° C. and 50° C.; or 50° C. and 70° C.; or the temperature setting is in the range of 10-50° C., preferably 20-40° C., more preferably 25-35° C. Pressure conditions are maintained at a reduced level of or below 8, 7, 6, preferably 5, 4, 3, more preferably 2, 1.5, 1, most preferably 0.8 or 0.5 mbar. These conditions are maintained for at least 1, 2, 3, 4, 5, 8, 10, 12, 16 or 24 hours.

Removing Solvent to Form a Foamed Glass

A subsequent stage of the foam drying method of the invention involves removing solvent until the foam dries to form a solid. In one embodiment of the invention, this is achieved by maintaining the pressure and temperature conditions at those applied in order to achieve foam formation. For instance, the pressure is maintained at or below 8, 7, 6, preferably 5, 4, 3, more preferably 2, 1.5, 1, most preferably 0.8 or 0.5 mbar while maintaining the temperature setting at a temperature above 0° C., preferably between 2° C. and 10° C., 10° C. and 20° C.; 20° C. and 30° C.; 30° C. and 35° C., 35° C. and 40° C. most preferably between 5° C. and 25° C. These temperature and pressure conditions are maintained for 1, 2, 3, 4, 5, 6, 8, 10, 12, 18 hours or more in order to obtain a solid with a solvent content less than or equal to 10, 8, 5, 4, preferably 3, 2 or most preferably 1% (w/w).

Another embodiment of the invention increases the temperature setting during solvent removal to a higher temperature setting than that maintained earlier in the process. This advantageously allows the solvent to leave the sample at a quicker rate so that the method of the invention can be completed in a shorter time. For instance, the temperature setting is increased to above 0° C., preferably between 2° C. and 10° C.; 10° C. and 20° C.; 20° C. and 30° C.; 30° C. and 40° C.; 40° C. and 50° C.; 50° C. and 60° C. while maintaining the pressure at or below 8, 7, 6, preferably 5, 4, 3, more preferably 2, 1.5, 1, most preferably 0.8 or 0.5 mbar. These temperature and pressure conditions are maintained for 1, 2, 3, 4, 5, 6, 8, 10, 12, 18 hours or more in order to obtain a solid with less than 10, 8, 5, 4, preferably 3, 2 or most preferably 1% (w/w) water content.

Another embodiment of the invention reduces the pressure setting during solvent removal to a lower pressure setting than that used during foam formation. This advantageously allows the solvent to leave the sample at a quicker rate so that the method of the invention can be completed in a shorter time. For instance, the pressure setting is decreased to at or below 5, 4, 3, preferably 2, 1, 0.8, more preferably 0.5, 0.1. most preferably 0.05 or 0.1 mbar, while maintaining the temperature at or above 0° C., preferably between 10° C. and 20° C.; 20° C. and 30° C.; 30° C. and 35° C. or above 40° C. These temperature and pressure conditions are maintained for 1, 2, 3, 4, 5, 6, 8, 10, 12, 18 hours or more in order to obtain a solid with a solvent content less than or equal to 5, 4, preferably 3 or 2 or more preferably 1% (w/w).

Foam Drying Including a Freezing Step

The method of the invention optionally involves freezing the sample. Freezing the sample prior to foam drying has the advantage of increased reproducibility between samples in a batch. This is due to all the samples starting the process from the same physical condition of being frozen. The preservation samples may be wholly or partially frozen.

Freezing is optionally carried out before subjected the sample to reduced pressure by placing the preservation sample at a temperature below 0° C. for a suitable amount of time to allow the sample to freeze. Preferably the temperature used is at or below −10° C., −15° C., −20° C., −30° C., −40° C., −70° C. or −140° C. The sample may be left at a temperature below 0° C. for 1, 2, 3, 4, 5, 8, 16 or more hours to allow freezing to occur.

For some samples, particularly samples that are easily damaged by solvent crystal formation such as cell preparations or other biological systems, it is preferable to freeze the sample slowly at a rate of less than or equal to 0.1, 0.5, 1, 2, 3, 4, 5° C. per hour. Other compositions are preserved more effectively by freezing instantaneously, for instance by snap freezing in liquid nitrogen. This method is particularly beneficial for proteins or viral particles. Freezing by evaporation also results in rapid freezing of the sample.

Alternatively, the preservation sample is frozen by subjecting the sample to reduced pressure such that the sample becomes wholly or partially frozen. Such quench freezing is carried out within a bulk freeze dryer apparatus, at a shelf temperature of or above 0° C., 10° C., 15° C., 20° C., 30° C., 37° C. Preferably the shelf temperature is between 5 and 35° C., more preferably between 10 and 20° C., most preferably at 15° C. The pressure is optionally reduced initially to 200 mbar for 5, 10, 20, 30, 60 minutes or more to allow degassing. In order to freeze the sample, the pressure is reduced further to a pressure equal to or below 2, 1, 0.5, 0.2, 0.1 mbar. This pressure is maintained for at least 5, 10, 20 or 30 minutes until the sample is wholly or partially frozen.

Subsequent steps of foam formation and removing solvent to form a solid are as described above.

In a preferred embodiment of the invention, the steps of freezing the sample within the freeze dryer and foam formation are performed at a constant temperature, preferably altering the pressure conditions.

In a further preferred embodiment the steps of freezing the sample within the freeze dryer, foam formation and solvent removal to form a solid, are performed at a constant temperature, preferably altering the pressure conditions.

In a further embodiment of the invention, both pressure and temperature conditions are different during the steps of freezing the sample, foam formation and solvent removal to form a solid.

The processes of the invention preferably use containers with a water repellent interior surface. This is achieved through coating the interior surface with a hydrophobic composition, for instance by siliconisation. Siliconisation is achieved by processes that are well known to those skilled in the art. Alternatively, the water repellent interior surface is achieved by the container being made of a water repellent composition.

The presence of a water repellent interior surface of the container makes foam formation more likely to occur and more reproducible. This allows lower polyol concentrations to be used in the preservation sample which in turn decreases the length of time necessary to dry the sample, reduces the effect of Maillard reactions or other harmful interactions between the polyol and the active agent. Where the preservation samples comprises a vaccine, the resultant solid is reconstituted quickly due to the lower amount of polyol present and the resultant vaccine solution is less viscous, allowing easier administration.

Drying without Freezing or Foam Formation

A particularly preferred method of the invention involves drying IPV in the presence of a stabilising agent, and preferably a bacterial polysaccharide, using a gentle process that avoids exposure of PV to freezing or foam formation so that IPV is subjected to less stress during the drying process and a high degree of antigenicity is retained.

This method is particularly applicable for use where a lower concentration of the glass forming polyol, for example at concentration below 10% (w/v), more preferably below 5% (w/v), is advantageous and a shorter drying time is preferred.

Loss of Solvent by Evaporation (Evaporative Drying—Step b)

The process of drying without freezing or foam formation involves subjecting the preservation sample to such pressure and temperature conditions so that the preservation sample looses solvent by evaporation, without the sample freezing or bubbling to form a foam.

The temperature within the preservation sample will, at times, be different from that external to the sample due to the endothermic nature of the evaporation process. References to temperature are to the conditions external to the preservation sample, for instance, where a large industrial freeze dryer is used, to the temperature of the shelf. This usually corresponds to the freeze dryer temperature setting.

Optionally a preliminary step of degassing the preservation sample is present in the method of the invention. The pressure is reduced to at or below 200 mBars, preferably between 200 and 35 mBars, for a period of at least 5 minutes before the pressure is reduced further.

A preferred embodiment of the invention achieves evaporative drying by reducing the pressure while controlling the temperature conditions. The pressure is adjusted to at or below 30, 25, 20, preferably 15, 12, most preferably 10, 8, 7, 6, 5, 4, 3, 2 or 1 mbar, while maintaining the temperature setting at a temperature above 0° C., preferably of between 4° C. to 37° C., 4° C. to 10° C., 10° C. to 15° C.; 15° C. to 20° C.; 20° C. to 25° C.; 25° C. to 30° C.; or 30° C. to 37° C.; or 37° C. to 45° C. These conditions are maintained for at least 1, 2, 3, 4, 5, 8, 10, 12, 16 or 24 hours, preferably for between 2-4 hours, 4-6 hours, 6-8 hours, 8-12 hours or 12-18 hours. In a particularly preferred embodiment, the pressure is maintained above 2 mbars where the temperature setting is 15° C. in order to prevent freezing of the sample. In a preferred embodiment, the temperature is maintained at 15° C. and the pressure is set to between 5-10 mBars, more preferably 6-9 mBars, most preferably around 8 mBars. Where a higher temperature setting is used, slightly lower pressure is possible without freezing the sample and where a lower temperature setting is used, the pressure should be maintained at the higher level to prevent freezing. Preferably the conditions are maintained for a sufficient period of time so that the evaporation rate has slowed so that the temperature of the sample is approximately the same as that external to the sample.

Preferably, the preservation sample should not freeze or boil to form a foam and looses solvent to form a viscous liquid or a highly viscous liquid.

Removing Solvent to Form a Highly Viscous Liquid

A subsequent stage of the method of the invention involves removing solvent until the preservation sample dries to form a highly viscous liquid without foam formation and preferably without freezing.

In one embodiment of the invention, this is achieved by maintaining the pressure and temperature conditions at those applied in the first evaporative drying stage. For instance, the pressure is maintained at or below at or below 30, 25, 20, preferably 15, 12, most preferably 10, 8, 7, 6, 5, 4, 3, 2 or 1 mbar, while maintaining the temperature setting at a temperature above 0° C., preferably of between 5° C. to 37° C., 5° C. to 10° C., 10° C. to 15° C.; 15° C. to 20° C.; 20° C. to 25° C.; 25° C. to 30° C.; or 30° C. to 37° C. For a temperature setting of 15° C., a pressure of 5-10 mBars, preferably 6-9 mBars, most preferably around 8 mBars is maintained for between 4-24 hours, preferably 1-4, 4-8, 8-12 or 12-16 hours. These temperature and pressure conditions are maintained for 1, 2, 3, 4, 5, 6, 8, 10, 12, 18 hours or more in order to obtain a highly viscous liquid with a solvent content less than or equal to 15, 12, preferably 10, 8, 5, 4, 3, 2 or 1% (w/w).

Another embodiment of the invention increases the temperature setting during solvent removal to a higher temperature setting than that maintained earlier in the process. This allows the solvent to leave the sample at a quicker rate so that the method of the invention can be completed in a shorter time. For instance, the temperature setting is increased to above 0° C., more preferably above 20° C., preferably between 5° C. and 37° C., 5° C. and 10° C., 10° C. and 20° C.; 20° C. and 30° C.; more preferably 30° C. and 40° C.; more preferably 40° C. and 50° C.; most preferably 50° C. and 60° C. while maintaining the pressure at or below 30, 25, 20, preferably 15, 12, most preferably 10, 8, 7, 6, 5, 4, 3, 2 or 1 mbar. These temperature and pressure conditions are maintained for 1, 2, 3, 4, 5, 6, 8, 10, 12, 18 hours or more in order to obtain a solid with less than or equal to 15, 12, preferably 10, 8, 5, 4, 3, 2 or 1%. This embodiment requires the active agent to be heat stable at the temperature used for the method to be carried out successfully.

A preferred embodiment of the invention reduces the pressure setting during solvent removal (step c) to a lower pressure setting than that used earlier in the process (step b). This allows the solvent to leave the sample at a quicker rate so that the method of the invention can be completed in a shorter time. It also enables a higher proportion of the solvent to be lost. For instance, the pressure setting is set to at or below 7, 6, preferably 5, 4, 3, more preferably 2, 1.5, 1, most preferably 0.8, 0.5, 0.2, 0.1, 0.05, 0.02, 0.01, or 0.005 mbar, while maintaining the temperature at or above 0° C., preferably between 10° C. and 20° C.; 20° C. and 30° C.; 30° C. and 35° C. or above 40° C. These temperature and pressure conditions are maintained for 1, 2, 3, 4, 5, 6, 8, 10, 12 or 18 hours or more in order to obtain a solid with a solvent content less than or equal to 15, 12, preferably 10, 8, 5, 4, 3, 2 or 1% (w/w) preferably as determined by Karl Fischer coulometric moisture analyser (Eur. J. Pharm. Biopharm. (2000) 50; 277-284).

Preferably, steps b) and c) should be completed in a time equal to or less than 18 hours, more preferably 16, 14, 12, most preferably 10, 8, 6 or 4 hours.

A dried composition is a composition from which solvent has been removed by evaporation, boiling, or sublimation leaving a solvent content less than or equal to 15, 12, 10, more preferably 8, 5, 4, 3, 2 or 1% (w/w), preferably as determined by the Karl Fischer method. Preferred ranges of solvent content are 1-3%, 3-5%, 5-10% or 10-15% (w/w). The term includes highly viscous liquids as well as dried foamed glass and lyophilised solids.

A highly viscous liquid is defined as a material from which solvent has been removed by evaporation without boiling, leaving a solvent content less than or equal to 15, 12, 10, preferably 8, 5, 4, 3, 2 or 1% (w/w), preferably as determined by the Karl Fischer method. Preferred ranges of solvent content are 1-3%, 3-5%, 5-10% or 10-15% (w/w). The highly viscous liquid has a sufficiently low solvent content such that the active agent is preserved in a stable state for at least 3,6,9,12 or 24 months at 4° C., allowing the active agent to retain at least 40, 50, 60, preferably 70, 80, 90 or 95% of its activity and/or antigenicity over this period. Preferably, the highly viscous liquid has a solid appearance but is a glass and is able to flow very slowly over a period of 2, 4, or 6 days, more preferably 1, 2, 3, 4, 6, 7, 10 or 12 months. The extremely slow flow may be measured by inverting a receptacle containing the highly viscous liquid and leaving at room temperature until the highly viscous liquid is observed to flow. In a preferred embodiment, the highly viscous liquid will not appear to flow after 2, 4 or 6 days, preferably 2, 3 or 4 weeks, more preferably 2, 4, 6, 8, 10 or 12 months in an inverted position.

A viscous liquid is defined as the product of the primary phase of solvent removal, at the end of which the majority of solvent has been lost from the sample. This point can be recognised because the rate of evaporation slows down so that the temperature of the sample returns to the ambient temperature as the endothermic effect of bulk evaporation is lost.

A foamed glass is a dried composition containing a glass forming polyol, which is formed by a method wherein the preservation sample is subjected to such temperature and pressure conditions that the sample bubbles vigorously or boils so that a foam is formed as the sample dries.

All references or patent applications cited within this patent specification are incorporated by reference herein.

EXAMPLES

The examples below are carried our using standard techniques, which are well known and routine to those of skill in the art, except where otherwise described in detail. The examples are illustrative, but do not limit the invention.

Example 1

Evaporative Freezing Process

The process was carried out using a Heto Drywinner 8-85 freeze-dryer in which shelf temperature maybe regulated to within 1° C., the final temperature of the condenser is −85° C., pressure is regulated with a bleed valve and 6 thermocouples are available to measure the product temperature.

Figure 1:
FIG. 1—Photographs of vials containing the preservation sample at different stages of the foam drying process.
Figure 1:
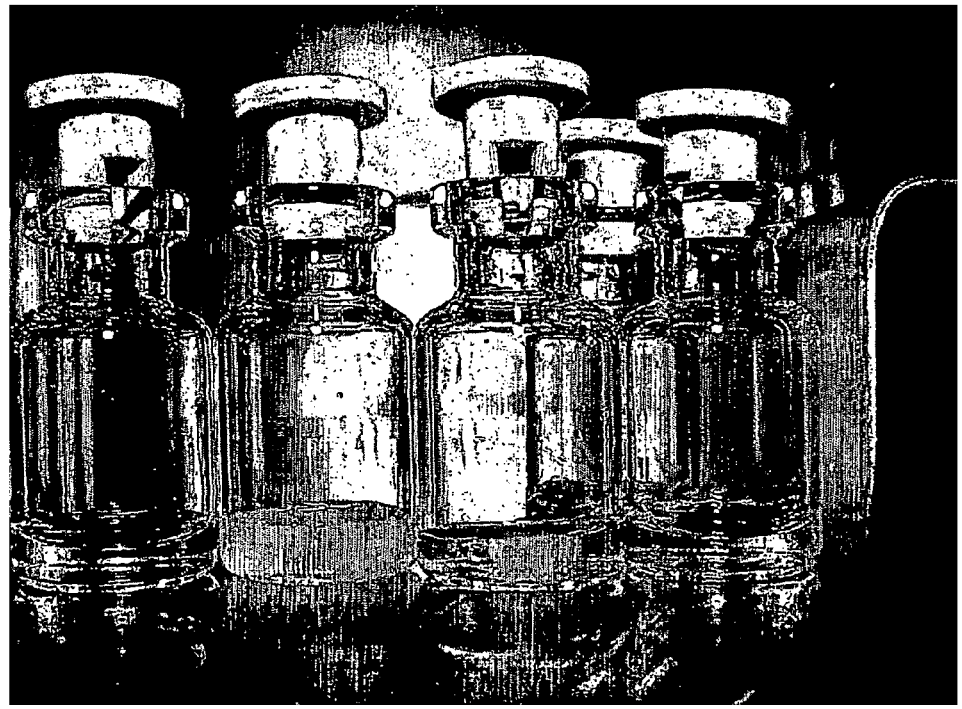
Figure 1:
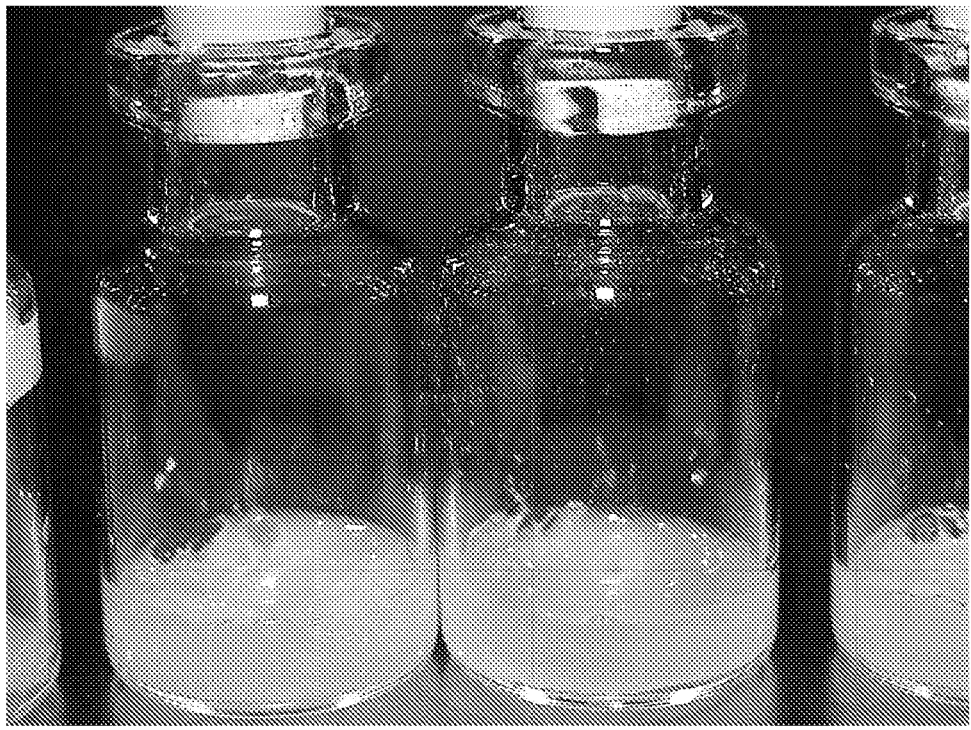
Figure 1:

A preservation sample was made by adding a stabilising agent (either 10% trehalose or 3.5% sucrose) and an active agent to an aqueous solution. Samples were put into the freeze dryer with a shelf temperature maintained at a fixed temperature setting of 15° C. throughout the process. The pressure was initially reduced to 200 mBar and maintained at this level for 10 minutes before reducing the pressure further. At 1.5 mBar, the solutions began to freeze due to evaporative cooling as shown in FIG. 1. The pressure is further reduced to 0.1 mBar to allow the samples to become fully frozen. The pressure was then increased to between 0.8 mBar and 3.5 mBar at which point a foam formed as water was lost from the sample. Under the conditions of the experiment, no boiling was seen in a control sample containing only water. The samples may be loosing water through evaporation rather than through boiling. After 18 hours under these conditions, the samples are dried and the foamed solution becomes a foamed glass.

A similar process was successfully performed keeping the shelf temperature at other temperature settings up to 37° C.

Example 2

Establishment of Freezing Conditions

Samples were made by dissolving sucrose in water to give 1%, 5%, 10% and 20% solutions. Samples were put into the freeze dryer with a shelf temperature maintained at 15° C. throughout the process. The pressure was initially reduced to 200 mBar and maintained at this level for 10 minutes before reducing the pressure further to 50 mBars, 5 mBars, 2.5 mBars, 0.75 mBars, 0.4 mBars and 0.2 mBars. Each pressure level was maintained for 20 minutes to allow the temperature to equilibrate and the temperature of the sample was read using a thermocouple. Thermocouples were attached to samples with different sucrose concentrations and the temperatures recorded in table 1 are mean values of the temperatures.

Results

All samples froze between 1.66 and 1.11 mbars, irrespective of the concentration of sucrose present. The temperatures measured at different pressures were very close to those predicted from the triple point curve. Therefore the presence of sucrose does not appear to have a large effect on the temperature of the samples at different pressures.

In a preferred method of the invention, it is necessary to avoid freezing of the sample. This could be achieved by maintaining the pressure above 2 mBars using a shelf temperature of 15° C. At lower temperatures the pressure should be maintained at a higher level whereas use of a higher temperature would allow the pressure to be reduced further without the samples freezing.

TABLE 1

| Pressure | Measured temperature | Theoretical temperature | Liquid/frozen |
|---|---|---|---|
| 1000 mBar | 15° C. | | liquid |
| 50 mBar | 15° C. | | liquid |
| 5 mBar | 1° C. | 1° C. | liquid |
| 2.5 mBar | −5° C. | −7° C. | liquid |
| 0.75 mBar | −21° C. | −21° C. | frozen |
| 0.4 mBar | −22° C. | −27° C. | frozen |
| 0.2 mBar | −27° C. | −32° C. | frozen |

Example 3

Foaming Conditions for Samples with Different Sugar Concentrations

Preservation samples containing 0%, 5%, 10%, 15%, 20%, 25% and 50% sucrose were made. Samples were put into the freeze dryer with a shelf temperature maintained at 15° C. throughout the process. The pressure was initially reduced to 200 mbars and maintained at this level for 10 minutes before reducing the pressure further. The pressure was further reduced to 0.1 mbars to allow the samples to become fully frozen. The pressure was then increased to either 0.788 mbars, 0.812 mbars or 3.5 mbars in subsequent experiment These conditions were maintained for 3 hours for the 3.5 mbars and 0.812 mbars experiments and for 6 hours for the 0.788 mbars experiment. The physical characteristics of each sample were evaluated.

Results

As shown in table 2, at a pressure of 3.5 mbars, a high sucrose concentration of 50% was required for reliable formation of foam. In contrast, a lower pressure of 0.8 mbars allowed reliable foam formation at lower sucrose concentrations of 10-25%. The use of lower sucrose concentration could be advantageous for preserved samples to be used in vaccines for instance. Therefore a process using 0.8 mbars and a 10-25% sucrose content is preferred.

TABLE 2

| Pressure | % sucrose | Physical characteristics |
|---|---|---|
| 3.5 mbars | 20 | ⅘ foamed, ⅕ viscous liquid |
| 3.5 mbars | 25 | ⅖ foamed, ⅗ viscous liquid |
| 3.5 mbars | 50 | 5/5 foamed |
| 0.812 mbars | 5 | Ring of crystallisation and bubbles |
| 0.812 mbars | 10 | All foamed |
| 0.812 mbars | 15 | All foamed |
| 0.812 mbars | 20 | All foamed |
| 0.812 mbars | 25 | All foamed |
| 0.788 mbars | 5 | Ring of crystallisation and bubbles |
| 0.788 mbars | 20 | All foamed |
| 0.788 mbars | 25 | All foamed |
| 0.788 mbars | 50 | Foam and syrup |

Example 4

The Effect of Using Siliconized Containers

Preservation samples containing 5%, 10%, 15% and 25% sucrose were made and added to vials, some of which were siliconized. In one experiment, samples were put into the freeze dryer with a shelf temperature maintained at 15° C. throughout the process. The pressure was initially reduced to 200 mbars and maintained at this level for 10 minutes before reducing the pressure further. The pressure was further reduced to 2.8 mbars for 3 hours. During this period, the pressure fell to 2.00 mbars as the presence of water vapour decreased. The physical characteristics of each sample were evaluated.

In a second experiment, samples were put into the freeze dryer with a shelf temperature maintained at 37° C. throughout the process. The pressure was initially reduced to 200 mbars and maintained at this level for 10 minutes before reducing the pressure further. The pressure was further reduced to 2.4 mbars for 3 hours. During this period, the pressure fell to 1.06 mbars as the presence of water vapour decreased. The physical characteristics of each sample were evaluated.

Results

Siliconization had an effect on the degassing of the samples. The reduction of pressure to 200 mbars resulted in degassing of samples in siliconized vials but not in unsiliconized vials. Degassing was seen by bubbling of the sample.

The siliconisation of the vial also made foam formation more likely to occur and more reproducible (table 3). Siliconisation of vials allows foam formation to occur reproducibly at lower polyol concentrations. The lower polyol concentration decreases the length of time necessary to dry the sample and reduces the effect of Maillard reactions or other interactions with the polyol harming the active agent. Where the sample involved is a vaccine, this reduces the viscosity of the sample and allows easier administration.

TABLE 3

| Temperature and pressure | % sucrose | Characteristics nonsiliconised vial | Characteristics siliconised vial |
|---|---|---|---|
| 15° C., 2.8 mbars | 5% | Viscous fluid | |
| 15° C., 2.8 mbars | 10% | Viscous fluid | foamed |
| 15° C., 2.8 mbars | 15% | Viscous fluid | |
| 15° C., 2.8 mbars | 25% | Viscous fluid | |
| 37° C., 2.4 mbars | 5% | 3 viscous fluid 2 foamed | |
| 37° C., 2.4 mbars | 10% | All viscous fluid | 5 foamed 1 viscous fluid |
| 37° C., 2.4 mbars | 15% | All foamed | |
| 37° C., 2.4 mbars | 25% | All foamed | |

Example 5

Comparison of Preservation of Hib-IPV by Conventional Freeze Drying or by Foam Drying The active agent to be preserved was a mixture of the PRP polysaccharide of *Haemophilus influenzae* b (Hib) and three strains of inactivated polio virus (IPV). The preservation sample was made by dissolving Hib-IPV in either a 3.15% sucrose solution or a 10% trehalose solution.

The samples were lyophilised either by using a conventional freeze drying sample that required three days to perform in a large freeze dryer, or by using the foam drying method described in example 1.

The samples were reconstituted in water and an ELISA was used to assess the retention of antigenicity of the three polio virus strains. Three polyclonal antibodies and three monoclonals, one against each strain, were used in separate ELISAs. Results are presented as a percentage of the reading given for a sample which had not undergone the freeze drying or foam drying procedure.

The preserved samples are assessed for their immunogenicity in vivo by inoculating groups of ten mice with the reconstituted IPV-Hib, withdrawing blood from the mice and monitoring levels of antibodies against IPV and Hib polysaccharides, for instance by ELISA or Western blotting. The degree of protection is assessed in a challenge mouse model.

Results

Using either sucrose or trehalose as the polyol, the antigenicity of IPV was maintained better using the foam drying technique compared to using conventional freeze drying.

TABLE 4

| Method of drying | Polyol content | ELISA - type 1/2/3 % | |
|---|---|---|---|
| | | Polyclonal | Monoclonal |
| Freeze drying | 3.15% sucrose | 46/49/58* | 25/0/0 |
| Foam drying | 3.15% sucrose | 85/97/106 | 55/68/57 |
| Freeze drying | 10% trehalose | 47/43/58 | |
| Foam drying | 10% trehalose | 93/86/84 | 72/75/87 |

*The experiment freeze drying in the presence of 3.15% sucrose was repeated five times and the results shown are from one representative experiment.

Example 6

Protective Effect of Freeze Drying IPV in the Presence of Hib Polysaccharides

Preservation samples were prepared containing 3.15% sucrose and IPV or a mixture of IPV and Hib polysaccharides. The samples were inserted into a Heto Drywinner 8-85 freeze-dryer and freeze dried at a temperature setting of −32° C. for 40 hours followed by continued drying at 4° C. for 16 hours.

The samples were reconstituted in water and an ELISA was used to assess the retention of antigenicity of the three polio virus strains. Three monoclonal antibodies, one against each strain, were used in separate ELISAs to assess the degree of antigen retention in the reconstituted, freeze dried sample compared to a reference sample that had not been frozen. Results are presented as a percentage of the reading given for a sample which had not undergone the freeze drying or foam drying procedure.

Results

As shown in table 5, the presence of Hib polysaccharide in the preservation sample with IPV, led to greater retention of IPV antigens after freeze drying than that achieved when IPV was freeze dried alone. The Hib polysaccharides have a preserving effect on IPV antigenicity in addition to that achieved by having sucrose present as a stabilising agent.

TABLE 5

| Composition freeze dried | Polyol content | ELISA - type 1/2/3 % |
|---|---|---|
| IPV | 3.15% sucrose | 26/25/0 |
| IPV-Hib | 3.15% sucrose | 52/68/0 |

Example 7

Effect of Different Stabilising Agents on Freeze Drying IPV-Hib

Preservations samples were made containing IPV-Hib and using either 3.15% sucrose; 2.5% sorbitol, 0.8% glutamine and 0.01% HSA; MMR stabiliser and lactose; 3% glycine, 2% arginine and 4% sucrose; or 4% sucrose and 2% glycine as stabilising agent. The experiment included a sample with 3.15% sucrose as stabilising agent using double the concentration of IPV-Hib. The samples were freeze dried using a conventional three day freeze drying cycle in a batch freeze dryer.

The samples were reconstituted in water and an ELISA was used to assess the retention of antigenicity of the three polio virus strains. Three polyclonal antibodies and three monoclonals, one against each strain, were used in separate ELISAs. Results are presented as a percentage of the reading given for a sample which had not undergone the freeze drying or foam drying procedure.

The preserved samples are assessed for their immunogenicity in vivo by inoculating groups of ten mice with the reconstituted IPV-Hib, withdrawing blood from the mice and monitoring levels of antibodies against IPV and Hib polysaccharides, for instance by ELISA or Western blotting. The degree of protection is assessed in a challenge mouse model.

Results

Increasing the dose of IPV from 40/8/32 DU/dose to 80/16/64 DU/dose led to an increase in retention of antigenicity of IPV as shown in table 6. Variation in the stabilising agent also influenced retention of antigens with 4% sucrose/2% glycine and 2.5% sorbitol/0.8% glutamine/0.01% HAS producing higher retention of antigens as shown by ELISA data.

TABLE 6

| Stabilising agent | Polyclonal ELISA results | Monoclonal ELISA results |
|---|---|---|
| 3.15% sucrose | 50/50/70 | 25/0/0 |
| 2.5% sorbitol 0.8% glutamine 0.01% HSA | 55/72/72 | 33/50/0 |
| MMR stabiliser lactose | 59/62/65 | 28/25/0 |
| 3.15% sucrose Double dose of IPV-Hib | 84/92/120 | 102/138/0 |
| 3% glycine 2% arginine 4% sucrose | | |
| 4% sucrose 2% glycine | 46/62/78 | 25/50/15 |

Example 8

Reproducibility of Sample Quality after Freeze Drying, Foam Drying or Foam Drying with a Freezing Step Preservation samples are made up comprising IPV, mumps, measles, rubella, varicella zoster virus, CMV, hepatitis, HSV1, HSV2, respiratory syncitial virus, dengue, paramyxoviridae such as parainfluenza, togaviridae and influenza viruses, and/or Hib as the active agent. The active agent is dissolved in an aqueous solution containing a polyol. Multiple samples are preserved by either freeze drying, foam drying using a freezing step following the protocol described in example 1, or foam drying without a freezing step using a protocol described in example 4. Samples are reconstituted in an aqueous solution and their activity assessed. This is accomplished using ELISA assays as described in example 5 using antibodies specific to native antigens. In the case of live viruses, the titre of each sample is established by using the virus to infect suitable host cells and assessing the infectivity by plaque formation or by immunocytochemistry. Where immunogenic compositions or vaccines are foam dried, the retention of immunogenicity can be tested in an animal model by immunising groups of animals with vaccine which is foam dried or freeze dried and boosting the immune response for instance at 14 and 28 days after the first immunisation. Serum is isolated from animals at the end of the immunisation schedule and its titre against the vaccine is tested using standard assays, for instance by ELISA, immunocytochemistry, Western blotting, immunoprecipitation, serum bacteriocidal assay or agglutination assay. Results are complied, first by comparing the activity of the active agent after freeze drying, foam drying with a freezing step, or foam drying without a freezing step. Secondly, the degree of reproducibility of the preservation technique is assessed by comparing the range of activities after subjecting samples to each of the three preservation methods.

Example 9

Long Term Storage of Active Agents Preserved by Freeze Drying, and Foam Drying

Preservation samples are made up comprising IPV, mumps, measles, rubella, varicella zoster virus, CMV, hepatitis, HSV1, HSV2, respiratory syncitial virus, dengue, paramyxoviridae such as parainfluenza, togaviridae and influenza viruses, and/or Hib as the active agent. The active agent is dissolved in an aqueous solution containing a polyol. Multiple samples are preserved by either freeze drying, foam drying using a freezing step following the protocol described in example 1, or foam drying without a freezing step using a protocol described in example 4. Samples are aged by storing at 37° C. or 23° C. for seven days and are compared for activity with samples that have been keep at 4° C. Samples are reconstituted in an aqueous solution and their activity assessed. This will be accomplished using ELISA assays as described in example 5 using antibodies specific to native antigens. In the case of live viruses, the titre of each sample is established by using the virus to infect suitable host cells and assessing the infectivity by plaque formation or by immunocytochemistry. Results are complied, first by comparing the activity of the active agent after storage at elevated temperatures with storage at 4° C. Secondly, the degree of reproducibility of the preservation technique is assessed by comparing the range of activities after subjecting samples to each set of conditions.

Example 10

Method for Drying without Freezing or Foam Formation

Preservation samples containing 5%, 10%, 15% and 25% sucrose were made and added to vials. Samples were put into a freeze dryer at a temperature setting of 15° C. throughout the process. The pressure was initially reduced to 200 mBars and maintained at this level for 10 minutes to allow degassing before reducing the pressure further. The pressure was further reduced to 8 mbars for two to three hours during which time thermocouples inside the samples showed that the sample temperature reduced to 4° C. due to evaporative cooling. After 2-3 hours, the temperature of the samples returned to 15° C., indicating that evaporation under these temperature and pressure conditions was near completion. During this stage of the process, the sample did not boil to form a foam or freeze so that an active agent within the sample is exposed to as little stress as possible. The samples have a solid appearance, similar to the final product.

Further drying of the samples was achieved by reducing the pressure further to 0.1 mbars while keeping the shelf temperature setting at 15° C. These conditions were maintained for a further 10-16 hours. During this phase, the sample temperature remained at 15° C. since the rate of evaporation was slow. Further drying took place and the resultant sample had a solid appearance. If the sample was place on its side, the sample contents slowed very slowly, over a period of days or months showing that the sample is a liquid glass of high viscosity. FIG. 2 shows that the containing holding the highly viscous liquid can be inverted without provoking immediate flow of the highly viscous liquid.

Example 11

Retention of IPV Immunogenicity after Drying without Freezing or Foam Formation

Samples dried according to the method of example 10 have not been subjected to stresses associated with the bubbling that accompanies foam formation or freezing. Experiments were performed to determine whether this method produced a high level of antigen retention when used to dry IPV.

Three separate experiments were performed in which IPV was resuspended in an aqueous solution with 10% sucrose or 10% trehalose as the stabilising agent. The samples were put into siliconised vials which were placed into a Heto Drywinner 8-85 freeze-dryer and the temperature was set to 15° C. The pressure was initially reduced to 35 mBars to degas the sample. After 10 minutes, the pressure was further reduced to 8 mBars and was kept at this level for two hours. During this period the temperature setting was kept at 15° C. and the temperature into the sample was monitored. As water evaporated from the sample, the temperature dropped to 4° C. but towards the end of the two hours, the temperature returned to 15° C. as the rate of evaporation slowed. No bubbling or foam formation occurred under these conditions. The pressure was then reduced further to 0.1 mbars and these conditions were maintained for 16 hours more in the first two experiments and for 10 hours more in the third experiment.

The samples were reconstituted in water and an ELISA was used to assess the retention of antigenicity of the three polio virus strains. The monoclonal antibody against type 3 IPV, was used in an ELISA to assess the degree of antigen retention in the reconstituted, freeze dried sample compared to a reference sample that had not been frozen. Results are presented as a percentage of the reading given for a sample which had not undergone a drying procedure.

Results

The dried samples had a solid appearance however they appeared to be in the form of a highly viscous liquid/glass since, over a period of days, the dried solid was able to flow if the container was inverted at room temperature.

TABLE 7

Retention of type 3 IPV antigen as determined by ELISA using a
monoclonal antibody (drying without foaming or freezing)

| Formulation | $1^{st}$ experiment (18 hour cycle) | $2^{nd}$ experiment (18 hour cycle) | $3^{rd}$ experiment (12 hour cycle) |
|---|---|---|---|
| 10% sucrose | 75% | 78% | 91% |
| 10% trehalose | 82% | 79% | 93% |

These levels of type 3 IPV antigen retention compares very favourably with the freeze drying results shown below where very low values were usually found in the same ELISA format when a monoclonal antibody against type 3 was used.

TABLE 8

Retention of type 1, 2 and 3 IPV antigens as determined by ELISA
using a monoclonal and polyclonal antibodies (freeze drying)

| | | ELISA - type 1/2/3 % | |
|---|---|---|---|
| Method of drying | Polyol content | Polyclonal | Monoclonal |
| Freeze drying | 3.15% sucrose | 46/49/58* | 19/25/0 |
| Freeze drying | 10% trehalose | 47/43/58 | 25/0/0 |

*The experiment freeze drying in the presence of 3.15% sucrose was repeated five times and the results shown are from one representative experiment.

Example 12

Long Term Storage stability of Dried IPV Stored as a Highly Viscous Liquid/Glass IPV dried using the method described in Example 11 was stored at 4° C. for 9 months. The samples were reconstituted in water with 150 mM NaCl and an ELISA was used to assess the retention of antigenicity of the three polio virus strains. Three monoclonal antibodies, one against each strain, were used in separate ELISAs to assess the degree of antigen retention in the reconstituted stored sample. A similar ELISA had been carried out on reconstituted samples from the same batch prior to storage. All results were compared to a reference sample that had not been dried. Results are presented as a percentage of the reading given for a sample which had not undergone a drying procedure.

Results

TABLE 9

Retention of IPV antigens after storage as a
highly viscous liquid for 9 months

| Treatment | Type 1 ELISA | Type 2 ELISA | Type 3 ELISA |
|---|---|---|---|
| Dried/reconstituted Not stored | 72% | 75% | 88% |
| Dried/reconstituted 9 months 4° C. | 70% | 94% | 90% |

Therefore IPV which has been dried by the method described in Example 11 can be stored at 4° C. for at least 9 months without loss of antigenicity.

Example 13

Comparison of the Immunogenicity in vivo of IPV after Drying to Form a Highly Viscous Liquid and Reconstitution Compared to Undried IPV Groups of 10 Wistar rats were inoculated with various dilutions of IPV which had been dried in the presence of 10% sucrose to form a highly viscous liquid using the method disclosed in Example 10 and reconstituted. Further groups of 10 Wistar rats were inoculated with reference samples of IPV which had been prepared in the same way but which had not been dried.

After 21 days, sera were taken from all the rats and the sera were tested in separate immunoprecipitation assays using Type 1, Type 2 and Type 3 polio virus.

Results are shown in table 10 that contains: —a) the number of responant rats for each IPV dilution, b) the ED50 which is the dose that is required to ensure that 50% of the rats seroconvert as assessed by the immunoprecipitation assay and c) the relative potency of the dried and reconstituted IPV compared to the undried reference IPV.

TABLE 10

Immunogenicity of IPV after drying to form a high
viscosity liquid (JLE017/05) and reconstitution
compared to an undried reference IPV (JLE097)

| Sample | Number of respondant | | | | ED50 | RP relative potency |
|---|---|---|---|---|---|---|
| | undiluted | 1/1.25 | 1/3.125 | 1/7.81 | | |
| JLE017/05 | | | | | | |
| Type 1 | 10 | 9 | 6 | 5 | 6.37 | 0.956 |
| Type 2 | 6 | 4 | 3 | 3 | 7.14 | 0.825 |
| Type 3 | 6 | 8 | 2 | 1 | 18.18 | 1.051 |
| JLE097 | | | | | | |
| Type 1 | 10 | 10 | 10 | 7 | 3.33 | 1.120 |
| Type 2 | 8 | 6 | 5 | 2 | 3.12 | 0.951 |
| Type 3 | 7 | 6 | 4 | 1 | 16.91 | 1.172 |
| Reference | | | | | | |
| Type 1 | | 10 | 8 | 4 | 6.37 | |
| Type 2 | | 7 | 5 | 2 | 2.93 | |
| Type 3 | | 5 | 3 | 0 | 22.57 | |

JLE017/05 is a IPV batch that was dried to form a highly viscous liquid and subsequently reconstituted. JLE097 is the undried reference.

Table 10 shows that the number of respondants inoculated with each dilution of IPV is similar between the two batches of dried and reconstituted IPV and the undried reference sample. In general, Type 1 IPV elicited the best immune response, with Type 2 eliciting an immune response in slightly fewer rats. Type 3 elicited the weakest immune response.

The process of drying to form a highly viscous liquid does not impair the ability of IPV to elicit immunoprecipitating antibodies in vivo. A relative potency (RP) reading of 1.0 indicates that the sample elicits an equivalent response to the reference sample. Both dried samples produce RP readings of close to 1.0 for all three types of polio virus indicating the drying process does not effect the ability of the sample to elicit an immune response.

Example 14

Effect of Drying to form a Highly Viscose Liquid Using Sucrose or Trehalose as Stabilising Agent on the Ability of IPV to Elicit an Immunoprecipitating Immune Response In Vivo Groups of 10 Wistar rats were inoculated with IPV which had been dried in the presence of either 10% sucrose or 10% trehalose as described in Example 2, and then reconstituted.

Further groups of 10 Wistar rats were inoculated with an equivalent amount of IPV that had not been dried, as reference samples.

After 21 days, sera were collected from all rats and an immunoneutralisation assay, as described in Example 5 was used to assess the amount of immunoneutralising antibody that had been raised against each of Type 1,Type 2 and Type 3 polio virus.

Relative potencies were calculated for each sample by comparing the immune response to that elicited by the undried reference sample.

Results are shown in Table 11.

TABLE 11

Comparison of drying in sucrose and trehalose

| Lot Number | Sugar present | Relative potency in vivo Type 1/ Type 2/Type 3 | Humidity % Karl Fischer | Duration (hours) |
|---|---|---|---|---|
| Jle017 | 10% trehalose | 0.95/0.82/1.05 | nd | 7 |
| 31CO3/01 | 10% sucrose | 0.69/1.20/0.97 | 4.6% | 18 |
| 31CO3/02 | 10% trehalose | 0.60/0.94/0.9 | 11.5% | 18 |
| 03D02/01 | 10% sucrose | 0.74/1.05/0.96 | 5.9% | 12 |
| 03D02/02 | 10% trehalose | 0.58/0.98/1.06 | 10.6% | 12 |

The amount of water remaining in samples was lower when sucrose was used as stabilising agent with approximately 5% humidity remaining compared to approximately 10% when trehalose was used as the stabilising agent measured by the Karl Fischer method.

Both sucrose and trehalose were effective at stabilising IPV during the drying process so that the reconstituted IPV gave relative potency readings approaching 1.0 for most of the different types of polio virus. The relative potencies were particularly good for Type 3 polio virus which looses its immunogenicity relatively easily.

Example 15

Measurement of Humidity by Karl Fischer

Analysis was carried out in a Karl Fischer titrometer (Aqua 30.00—Elektrochemie Halle). The sample was weighed out and placed into the oven at a setting of 80° C. The sample was flushed with nitrogen gas and then added to hydranal reagent (Riedel de Hahn) in order to perform the analysis by coulometry.

The invention claimed is:

1. An immunogenic composition comprising:
   (a) inactivated polio virus (IPV) comprising type 1, type 2, and type 3 polio virus,
   (b) a capsular polysaccharide or oligosaccharide antigen from *Haemophilus influenzae* b, and
   (c) a stabilizing agent,
   all formulated as a dried composition, which after reconstitution is capable of generating an immune response against polio virus,
   wherein the antigenicity of type 1, type 2, and type 3 polio virus is retained at a level of at least 40% of the antigenicity of a reference sample which has not been formulated as a dried composition, and
   wherein the stabilizing agent comprises a glass-forming polyol selected from the group consisting of: trehalose, sucrose, sorbitol, raffinose, mannitol, lactose, lactitol, or palatinit.

2. The immunogenic composition of claim 1, wherein the polysaccharide or oligosaccharide is conjugated to a carrier protein.

3. The immunogenic composition of claim 2, wherein the polysaccharide or oligosaccharide is conjugated to tetanus toxoid.

4. The immunogenic composition of claim 1, wherein the polysaccharide or oligosaccharide is adsorbed onto aluminium phosphate.

5. The immunogenic composition of claim 1, further comprising phenol red.

6. The immunogenic composition of claim 1, wherein the dried composition is freeze dried.

7. The immunogenic composition of claim 1, wherein the dried composition is a foamed glass.

8. The immunogenic composition of claim 1, wherein the dried composition is a highly viscous liquid.

9. The immunogenic composition of claim 8, wherein the highly viscous liquid has not been frozen.

10. A kit comprising the immunogenic composition of claim 1, in one container and liquid acellular or whole cell diphtheria, tetanus and *Bordetella pertussis* (DTP) vaccine in a second container.

11. The kit of claim 10, further comprising Hepatitis B surface antigen in the second container.

12. A vaccine comprising the immunogenic composition of claim 1.

13. A container with a water repellent internal surface containing the vaccine of claim 12.

* * * * *